United States Patent [19]
Godel et al.

[11] Patent Number: 5,688,798
[45] Date of Patent: Nov. 18, 1997

[54] PYRIMIDINE COMPOUNDS

[75] Inventors: Thierry Godel, Basel, Switzerland; Claus Riemer, Freiburg, Germany

[73] Assignee: Hoffmann-La Roche Inc., Nutley, N.J.

[21] Appl. No.: 714,030

[22] Filed: Sep. 11, 1996

[30] Foreign Application Priority Data

Oct. 10, 1995 [CH] Switzerland ............................. 2855/95
Jun. 28, 1996 [CH] Switzerland ............................. 1625/96

[51] Int. Cl.[6] .................... A61K 31/505; C07D 239/28
[52] U.S. Cl. .................... 514/256; 514/275; 544/242; 544/322; 544/324; 544/330; 544/331; 544/333; 544/335; 544/328
[58] Field of Search ............................. 544/242, 322, 544/324, 328, 330, 331, 333, 335; 514/256, 275

[56] References Cited

U.S. PATENT DOCUMENTS 3,060,184  10/1962  Clark et al. .......................... 260/256.4
3,155,572  11/1964  Rogers et al. ........................ 167/53.1

FOREIGN PATENT DOCUMENTS 0 096 214  12/1983  European Pat. Off. .
0 449 186  10/1991  European Pat. Off. .
0 499 187  10/1991  European Pat. Off. .
94/20459   9/1994   WIPO ................................ 514/256

OTHER PUBLICATIONS

CA 100: 139135z Antibacterial Pyrimidine Compounds. Daluge et al., p. 655, 1984.
CA 83: 202327m Effects of . . . Antimetabolites. Goldberg et al, p. 73, 1975.
CA 83: 202326k Effects of . . . Potentials. Goldberg et al., p. 72, 1975.
CA 70: 75399r Effects of . . . Capsulatum. McVeigh et al., p. 107, 1969.
TiPS, Jul. 1994, vol. 15, pp. 264–270, Seeman et al.

*Primary Examiner*—Joseph McKane
*Attorney, Agent, or Firm*—George W. Johnston; Ellen Ciambrone Coletti; Robert A. Silverman

[57] ABSTRACT

Compounds of the formula wherein $R^1$ and $R^2$ each individually are lower-alkyl or amino,
A is $A^1$   $A^2$ $A^3$   $A^4$ $A^5$   $A^6$ or $A^7$ ;

B is hydrogen in $A^4$, $A^5$ and $A^6$;

—$(CH_2)_p$—$(O)_m$—$(CH_2)_n$— in $A^1$-$A^6$;
lower-alkoxy in $A^4$-$A^6$;
and lower-alkyl, styryl, phenylethynyl or benzoyloxy-lower-alkyl in $A^1$ and $A^2$;

n is 0, 1 or 2;
m, p are, independently 0, 1 and
$R^3$, $R^4$, $R^5$ and $R^6$ each independently are hydrogen, halogen, lower-alkyl, trifluoromethyl, lower-alkoxy or nitro, and pharmaceutically acceptable acid addition salts thereof. These compounds are useful in the control or prevention of illnesses which are caused by disorders of the dopamine system, in particular psychotic illnesses such as schizophrenia.

16 Claims, No Drawings

PYRIMIDINE COMPOUNDS

SUMMARY OF THE INVENTION

The invention relates to pyrimidine compounds of the formula

[Structure I: pyrimidine with R¹, R², A substituents]

I and pharmaceutically acceptable salts of compounds of formula I.

DETAILED DESCRIPTION OF THE INVENTION

Preferred compounds of formula I and salts thereof include compounds of the formula:

[Structure IA¹]

a)

wherein
B is

[Structure: $-(CH_2)_p-(O)_m-(CH_2)_n-$ phenyl with $R^3, R^4, R^5, R^6$]

lower-alkyl, styryl, phenylethynyl or benzoyloxy-lower-alkyl;

$R^1$ and $R^2$ are, independently, lower-alkyl or amino; $R^3-R^6$ are independently hydrogen, halogen, lower-alkyl, trifluoromethyl, lower-alkoxy or nitro;

m, p are, independently, 0 or 1 and is 0, 1 or 2;

b)

[Structure IA²]

wherein
B is

[Structure: $-(CH_2)_p-(O)_m-(CH_2)_n-$ phenyl with $R^3, R^4, R^5, R^6$]

lower-alkyl, styryl, phenylethynyl or benzoyloxy-lower-alkyl;

$R^1$ and $R^2$ are, independently, lower-alkyl or amino;
$R^3-R^6$ are, independently hydrogen, halogen, lower-alkyl, trifluoromethyl, lower-alkoxy or nitro;
n is 0, 1 or 2, and m, p are, independently, 0 or 1;

c)

[Structure IA³]

wherein
B is

[Structure: $-(CH_2)_p-(O)_m-(CH_2)_n-$ phenyl with $R^3, R^4, R^5, R^6$]

$R^1$ and $R^2$ are, independently, lower-alkyl or amino; $R^3-R^6$ are independently hydrogen, halogen, lower-alkyl, trifluoromethyl, lower-alkoxy or nitro;

n is 0, 1 or 2, and m, p are, independently, 0 or 1;

d)

[Structure IA⁴]

[Structure IA⁵]

and

[Structure IA⁶]

wherein

B is hydrogen, lower-alkoxy or

[Structure: $-(CH_2)_p-(O)_m-(CH_2)_n-$ phenyl with $R^3, R^4, R^5, R^6$]

$R^1$ and $R^2$ are, independently, lower-alkyl or amino;

$R^3-R^6$ are, independently, hydrogen, halogen, lower-alkyl, trifluoromethyl, lower-alkoxy or nitro;

n is 0, 1 or 2, and m, p are, independently, 0 or 1;

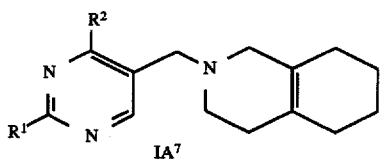

wherein

R¹ and R² are independently, lower-alkyl or amino.

The compounds of formula I and salts thereof possess valuable pharmacological properties.

It has been found that these compounds are useful for the control or prevention of illnesses which are caused by disorders of the dopamine system. In particular, these compounds are useful for the treatment or prevention of psychotic illnesses such as schizophrenia.

Objects of the present invention are the aforementioned compounds of formula I and salts thereof per se and as therapeutically active substances, their manufacture and their use for therapeutic purposes and, respectively, for the production of corresponding medicaments as well as medicaments containing a compound of formula I or a salt thereof and the production of such medicaments for the said purpose.

The term "lower" denotes residues or compounds with a maximum of 7, preferably up to 4, carbon atoms. The term "alkyl" denotes straight-chain or branched saturated hydrocarbon groups such as methyl, ethyl, n-propyl, iso-propyl, n-butyl, sec.-butyl, iso-butyl or tert.-butyl. The term "alkoxy" denotes an alkyl group bonded via an oxygen atom, such as methoxy or ethoxy. The term "halogen" embraces fluorine, chlorine, bromine or iodine. The term "reactive leaving group" preferably denotes a halogen, e.g. chlorine or bromine, or an activated hydroxy group.

Compounds in which R¹ signifies methyl, R² signifies amino, A signifies A² and B signifies phenethyl, styryl or phenyl substituted by chlorine or methoxy are preferred.

Examples of such compounds are:

5- [4-(4-Chloro-phenyl)-3,6-dihydro-2H-pyridin-1-ylmethyl]-2-methyl-pyrimidin-4-ylamine;

5-[4-(4-methoxy-phenyl)-3,6-dihydro-2H-pyridin-1-ylmethyl]-2-methyl-pyrimidin-4-ylamine;

2-methyl-5-(4-phenethyl-3,6-dihydro-2H-pyridin-1-ylmethyl)-pyrimidin-4-ylamine; and (E)-2-methyl-5-(4-styryl-3,6-dihydro-2H-pyridin-2-ylmethyl)-pyrimidin-4-ylamine.

Furthermore, compounds in which R¹ signifies methyl, R² signifies amino, A signifies A⁴ or A⁷ and B in A⁴ signifies hydrogen or unsubstituted phenyl are preferred, especially 5-(3,4,5,6,7,8-hexahydro-1H-isoquinolin-2-ylmethyl)-2-methyl-pyrimidine-4-ylamine and 2-methyl-5-(6-phenyl-3,4-dihydro-1H-isoquinolin-2-ylmethyl)-pyrimidin-4-ylamine.

The aforementioned compounds of formula I and their pharmaceutically acceptable salts can be manufactured in accordance with the invention by a) reacting a compound of the general formula

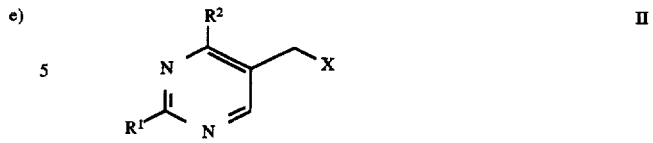

or a salt thereof,
wherein R¹ and R² have the significance set forth above and X signifies a reactive leaving group,
with a compound of the general formula

H—A    III wherein A has the significance set forth above, or b) hydrogenating a compound of formula I in which A signifies A² and all other substituents have the significance set forth above, to compounds of formula I in which A signifies A³, or c) reducing a compound of the formula

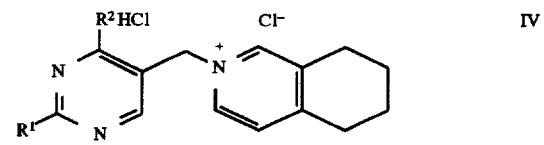

wherein R¹ and R² have the significance set forth above, to a compound of formula I in which A signifies A⁷, or d) converting a compound of general formula I into a pharmaceutically usable acid addition salt.

In accordance with process variant a) compounds of formula I are obtained by reacting a compound of formula II or a salt thereof, which contains a reactive leaving group, with a compound of formula III. The leaving group is conveniently a halogen atom, preferably chlorine or bromine.

The reaction is conveniently effected in the presence of an inert solvent such as N,N-dimethylformamide and in the presence of a base such as, for example, a tertiary amine such as triethylamine or in the presence of, for example, potassium carbonate. Conveniently, the reaction is effected under a protective gas atmosphere in a temperature range of room temperature to 130° C. and, depending on the reaction partners, within one hour to 110 hours. Preferred reaction conditions will be described in more detail in the working Examples.

When X in formula II signifies a hydroxy group as the leaving group, this compound is dissolved in an inert solvent, for example tetrahydrofuran, and treated under a protective gas atmosphere at about −78° C. with butyl-lithium and 4-methyl-benzenesulphonyl chloride and in the presence of a tertiary amine with a compound of formula III.

In accordance with process variant b) a compound of formula I in which A signifies A³ can be obtained by hydrogenating a compound of formula I in which A signifies A². The hydrogenation is effected according to generally known methods, with platinum dioxide conveniently being used as the catalyst and the catalyst being dissolved in an inert solvent, for example tetrahydrofuran, and treated with a solution of the compound to be hydrogenated and tetrahydrofuran. The hydrogenation is effected under normal pressure.

Compounds of formula I in which A signifies A⁷ are obtained by reduction in accordance with process variant c).

This process will be described in more detail in the following example: A methanolic solution of the compound 2-(4-amino-2-methyl-pyrimidin-5-ylmethyl)-5,6,7,8-tetrahydroisoquinolinium chloride hydrochloride, obtained according to Example 24 a), is treated with sodium borohydride at about 10° C. The reaction has finished after a reaction period of about 1 hour and subsequently the reaction product can be worked-up to the desired pure product according to conventional methods. The compounds of formula I can be converted into pharmaceutically acceptable acid addition salts in accordance with process variant d). Not only salts with inorganic acids, but also salts with organic acids come into consideration. Examples of such salts are the hydrochlorides, hydrobromides, sulphates, nitrates, citrates, acetates, maleates, succinates, methanesulphonates, p-toluenesulphonates and the like. These salts can be prepared according to known methods and which are familiar to those skilled in the art.

The starting materials of formulae II and III are commercial products or can be prepared according to known methods. One route to a compound of formula III is described in Example 27.

The compounds of formula I possess valuable pharmacological properties and have only a very low toxicity. They have as a common characteristic a high selective affinity to a neuroreceptor, especially to the dopamine $D_4$ receptor. Thereby, it can be expected that when these compounds are used significantly fewer side effects will occur than in the case of known classical neuroleptic agents which, as is known, bind to the $D_2$ or $D_3$ receptor, for example haloperidol. It has been found that in the case of schizophrenia the $D_2$ and $D_3$ receptor density increases by 10%, while it can increase in the case of the $D_4$ receptor by 600% (TIPS, July 1994, Vol. 15, p. 264–70).

Test description

The compounds were characterized by their binding behaviour at the $D_4$ receptor.

CHO cells (Chinese Hamster Ovary) were used in the test. Crude membranes were isolated by ultracentrifugation from $D_4$-CHO and $D_2$-CHO cells and were stored at −80° C. After thawing and homogenizing in a buffer solution (50 mM Tris, 1 mM EDTA, 5 mM KCl, 1.5 mM $CaCl_2$, 4 mM $MgCl_2$, pH 7.4) they were incubated at room temperature for 90 minutes with 200 pM [3H]-spiperone and an increasing concentration ($1\times10^{-11}$M to $1\times10^{-4}$M) of the test compound. A non-specific binding was established by incubating in the presence of $1\times10^{-5}$M (+)-butaclamol. The unbound radioligand was removed by filtration through a GF/C glass filter and the bound radioactivity was determined by scintillation in a Packard TopCount.

The following Table shows the binding behaviour of some selected compounds at the $D_4$ receptor. The Ki value is a binding constant which shows the affinity of the compounds to the $D_4$ receptor. It was determined using :$^3$H-spiperone. The calculation of the value was effected with ligand.

| Compound/Example No. | | Affinity to dopamine $D_4$ receptors, Ki [nM] |
|---|---|---|
| A | 3 | 33 |
| B | 7 | 28 |
| C | 14 | 8.3 |
| D | 15 | 9.3 |
| E | 16 | 4.7 |
| F | 17 | 5.4 |
| G | 19 | 0.4 |
| H | 21 | 6.2 |
| I | 22 | 23 |

-continued

| Compound/Example No. | | Affinity to dopamine $D_4$ receptors, Ki [nM] |
|---|---|---|
| J | 24 | 7.8 |
| K | 28 | 1.3 |
| L | 29 | 0.9 |
| M | 33 | 14 |
| N | 41 | 30 |
| O | 42 | 14 |

A 5-[4-(4-Chloro-phenyl)-piperazin-1-ylmethyl]-2-methyl-pyrimidin-4-ylamine
B 5-[4-(3-Chloro-phenyl)-piperazin-1-ylmethyl]-2-methyl-pyrimidin-4-ylamine
C 5-(4-Phenyl-3,6-dihydro-2H-pyridin-1-ylmethyl)-2-methyl-pyrimidin-4-ylamine
D 5-[4-(4-Fluoro-phenyl)-3,6-dihydro-2H-pyridin-1-ylmethyl]-2-methyl-pyrimidin-4-ylamine
E 5-[4-(4-Chloro-phenyl)-3,6-dihydro-2H-pyridin-1-ylmethyl]-2-methyl-pyrimidin-4-ylamine
F 5-[4-(4-Methoxy-phenyl)-3,6-dihydro-2H-pyridin-1-ylmethyl]-2-methyl-pyrimidin-4-ylamine
G 2-Methyl-5-(6-phenyl-3,4-dihydro-1H-isoquinolin-2-ylmethyl)-pyrimidin-4-ylamine
H 2-Methyl-5-(7-phenyl-3,4-dihydro-1H-isoquinolin-2-ylmethyl)-pyrimidin-4-ylamine
I 5-(7-Benzyloxy-3,4-dihydro-1H-isoquinolin-2-ylmethyl]-2-methyl-pyrimidin-4-ylamine
J 5-(3,4,5,6,7,8-Hexahydro-1H-isoquinolin-2-ylmethyl)-2-methyl-pyrimidin-4-ylamine
K 2-Methyl-5-(4-phenethyl-3,6-dihydro-2H-pyridin-1-ylmethyl)-pyrimidin-4-ylamine
L (E)-2-Methyl-5-(4-styryl-3,6-dihydro-2H-pyridin-1-ylmethyl)-pyrimidin-4-ylamine
M 5-[4-(2-Methoxy-phenyl)-piperazin-1-ylmethyl]-2-propyl-pyrimidin-4-ylamine
N 5-[4-(2-Methoxy-phenyl)-piperazin-1-ylmethyl]-pyrimidine-2,4-diamine
O 5-(4-Phenyl-3,6-dihydro-2H-pyridin-1-ylmethyl)-pyrimidine-2,4-diamine.

The compounds of formula I and pharmaceutically acceptable salts thereof can be used as medicaments, for example, in the form of pharmaceutical preparations. The pharmaceutical preparations can be administered orally, for example, in the form of tablets, coated tablets, dragées, hard and soft gelatine capsules, solutions, emulsions or suspensions. The administration can, however, also be effected rectally, for example, in the form of suppositories, or parentally, for example, in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Adjuvants such as alcohols, polyols, glycerol, vegetable oils and the like can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention. Also a process for the production of such medicaments, which comprises bringing one or more compounds of formula I or pharmaceutically acceptable salts thereof and, if desired, one or more other-therapeutically valuable substances into a galenical administration form together with one or more therapeutically inert carriers are also an object of the present invention. The dosage can vary within wide limits and will, of course, be fitted to the individual requirements in each particular case. In general, a daily dosage of about 1 mg to 100 mg should be appropriate.

Finally, as mentioned earlier, the use of compounds of formula I and of pharmaceutically usable salts thereof for the production of medicaments, especially for the control or prevention of illnesses which are caused by disorders of the dopamine system, is also an object of the invention.

The following Examples are intended to illustrate the invention in more detail, but without being limiting.

EXAMPLE 1

2-Methyl-5-(4-phenyl-piperazin-1-ylmethyl)-pyrimidin-4-ylamine a) A suspension of 0.233 g (0.001 2 mol) of 5-chloromethyl-2-methyl-pyrimidin-4-ylamine hydrochloride in 5 ml of dimethylformamide was treated with 0.5 ml (0.0036 mol) of triethylamine and 0.22 ml (0.00144 mol) of 1-phenyl-piperazine and the mixture was stirred at room temperature under argon for 3 hours. The mixture was completely freed from the solvents and the residue was triturated in 5 ml of water. The resulting crystals were filtered off under suction, dried and chromatographed over silica gel with dichloromethane/methanol 19:1 as the eluent. 0.22 g of a colourless solid was obtained.

b) The product was suspended in 5 ml of methanol and treated with excess hydrochloric acid in diethyl ether. Crystals separated from the resulting solution. The suspension was completely freed from the solvents and recrystallized from methanol/diethyl ether. 0.22 g (52%) of 2-methyl-5-(4-phenyl-piperazin-1-ylmethyl)-pyrimidin-4-ylamine dihydrochloride was obtained as white crystals; m.p. 255°–260°.

EXAMPLE 2

5-[4-(4-Fluoro-phenyl)-piperazin-1-ylmethyl]-2-methyl-pyrimidin-4-ylamine a) A suspension of 0.31 5 g (0.0020 mol) of 5-chloromethyl-2-methyl-pyrimidin-4-ylamine in 5 ml of dimethylformamide was treated with 0.76 g (0.0042 mol) of 1-(4-fluoro-phenyl)-piperazine and the mixture was stirred at room temperature under argon for 1 hour. The mixture was completely freed from the solvents and the residue was triturated in 5 ml of water. The resulting crystals were filtered off under suction, dried and chromatographed over silica gel with dichloromethane/methanol 19:1 as the eluent. 0.30 g of a colourless solid was obtained.

b) The product was suspended in 5 ml of methanol and treated with excess hydrochloric acid in diethyl ether. Crystals separated from the resulting solution. The suspension was completely freed from the solvents and recrystallized from methanol. 0.25 g (33%) of 5-[4-(4-fluoro-phenyl)-piperazin-1-ylmethyl]-2-methyl-pyrimidin-4-ylamine dihydrochloride was obtained as white crystals; m.p. 248°–254°.

EXAMPLE 3

5-[4-(4-Chloro-phenyl)-piperazin-1-ylmethyl]-2-methyl-pyrimidin-4-ylamine a) A suspension of 0.19 g (0.001 2 mol) of 5-chloromethyl-2-methyl-pyrimidin-4-ylamine and 0.51 g (0.0018 mol) of 1-(4-chloro-phenyl)-piperazine dihydrochloride in 5 ml of dimethyl-formamide was treated with 0.7 ml (0.0050 mol) of triethylamine and the mixture was stirred at room temperature under argon for 1.5 hours. The mixture was completely freed from the solvents and the residue was triturated in 25 ml of water. The resulting crystals were filtered off under suction, dried and chromatographed over silica gel with dichloromethane/methanol 19:1 as the eluent. 0.18 g of a colourless solid was obtained.

b) The product was suspended in 3 ml of methanol and treated with excess hydrochloric acid in diethyl ether. Crystals separated from the resulting solution. The suspension was completely freed from the solvents and recrystallized from methanol/diethyl ether. 0.125 g (27%) of 5-[4-(4-chloro-phenyl)-piperazin-1-ylmethyl]-2-methyl-pyrimidin-4-ylamine dihydrochloride was obtained as white crystals; m.p. 230°–240°.

EXAMPLE 4

2-Methyl-5-(4-p-tolyl-piperazin-1-ylmethyl)-pyrimidin-4-ylamine a) A suspension of 0.233 g (0.0012 mol) of 5-chloromethyl-2-methyl-pyrimidin-4-ylamine hydrochloride in 5 ml of dimethylformamide was treated with 0.5 ml (0.0036 mol) of triethylamine and 0.253 g (0.00144 mol) of 1-p-tolyl-piperazine and the mixture was stirred at room temperature under argon for 3 hours. The mixture was completely freed from the solvents and the residue was triturated in 5 ml of water. The resulting crystals were filtered off under suction, dried and chromatographed over silica gel with dichloromethane/methanol 19:1 as the eluent. 0.25 g of a colourless solid was obtained.

b) The product was suspended in 5 ml of methanol and treated with excess hydrochloric acid in diethyl ether. Crystals separated from the resulting solution. The suspension was completely freed from the solvents and recrystallized from methanol/diethyl ether. 0.305 g (63%) of 2-methyl-5-(4-p-tolyl-piperazin-1-ylmethyl)-pyrimidin-4-ylamine trihydrochloride was obtained as white crystals; m.p. 275°–278°.

EXAMPLE 5

2-Methyl-5-[4-(4-trifluoromethyl-phenyl)-piperazin-1-ylmethyl-pyrimidin-4-ylamine a) A suspension of 0.233 g (0.0012 mol) of 5-chloromethyl-2-methyl-pyrimidin-4-ylamine hydrochloride in 5 ml of dimethylformamide was treated with 0.5 ml (0.0036 mol) of triethylamine and 0.33 g (0.00144 mol) of 1-(4-trifluoromethyl-phenyl)-piperazine and the mixture was stirred at room temperature under argon for 3 hours. The mixture was completely freed from the solvents and the residue was triturated in 5 ml of water. The resulting crystals were filtered off under suction, dried and chromatographed over silica gel with dichloromethane/methanol 19:1 as the eluent. 0.36 g of a yellowish solid was obtained.

b) The product was suspended in 5 ml of methanol and treated with excess hydrochloric acid in diethyl ether. Crystals separated from the resulting solution. The suspension was completely freed from the solvents and recrystallized from methanol. 0.25 g (49%) of 2-methyl-5-[4-(4- trifluoromethyl-phenyl)-piperazin-1-ylmethyl]-pyrimidin-4-ylamine hydrochloride (1:1.85) was obtained as whited crystals; m.p. 254°–259°.

EXAMPLE 6

5-[4-(4-Methoxy-phenyl)-piperazin-1-ylmethyl]-2-methyl-pyrimidin-4-ylamine a) A suspension of 0.19 g (0.0012 mol) of 5-chloromethyl-2-methyl-pyrimidin-4-ylamine in 5 ml of dimethylformamide was treated with 0.7 ml (0.0050 mol) of triethylamine and 0.53 g (0.0018 mol) of 1-(4-methoxy-phenyl)-piperazine and the mixture was stirred at room temperature under argon for 5 hours. The reaction mixture was poured into 25 ml of water, suction filtered, the resulting crystals were dried and chromatographed over silica gel with dichloromethane/methanol 19:1 as the eluent. 0.175 g of a colourless solid was obtained.

b) The product was suspended in 3 ml of methanol and treated with excess hydrochloric acid in diethyl ether. Crystals separated from the resulting solution upon cooling. The crystals were filtered off under suction and dried in a vacuum. 0.125 g (27%) of 5-[4-(4-methoxy-phenyl)-piperazin-1-ylmethyl]-2-methyl-pyrimidin-4-ylamine hydrochloride (1:2.25) was obtained as white crystal; m.p. 245°–247°.

EXAMPLE 7

5-[4-(3-(Chloro-phenyl)-piperazin-1-ylmethyl]2-methyl-pyrimidin-4-ylamine a) A suspension of 5.82 g (0.030 mol) of 5-chloromethyl-2-methyl-pyrimidin-4-ylamine hydrochloride in 60 ml of dimethyl-formamide was treated with 10 g (0.072 mol) of dry potassium carbonate. At the same time, a suspension of 8.1 g (0.030 mol) of 1-(3-chloro-phenyl)-piperazine hydrochloride was treated with 10 g (0.072 mol) of dry potassium carbonate in 60 ml of dimethylformamide. After stirring at room temperature for ¾ hours both solutions were combined and stirred for a further 4 hours. The reaction mixture was suction filtered, the mineral salt was washed firstly with dichloromethane, then with ethanol, and chromatographed over silica gel with dichloromethane/ethyl acetate 1:1 as the eluent. 3.4 g of a colourless solid were obtained. An analytical sample was recrystallized from hot ethanol and gave 5-[4-(3-chloro-phenyl)-piperazin-1-ylmethyl]-2-methyl-pyrimidin-4-ylamine as beige crystals; m.p. 245°–248°.

b) The product was dissolved in methanol and treated with an excess of hydrochloric acid in diethyl ether. Crystals separated from the resulting solution upon cooling. The crystals were filtered off under suction and dried in a vacuum. 2.3 g (20%) of 5-[4-(3-chloro-phenyl)-piperazin-1-ylmethyl]-2-methyl-pyrimidin-4-ylamine dihydrochloride were obtained as yellowish crystals; m.p. 286°–289°.

EXAMPLE 8

2-Methyl-5-(4-m-tolyl-piperazin-1-ylmethyl)-pyrimidin-4-ylamine a) A suspension of 0.233 g (0.001 2 mol) of 5-chloromethyl-2-methyl-pyrimidin-4-ylamine hydrochloride in 5 ml of dimethylformamide was treated with 0.36 g (0.00144 mol) of 1-m-tolyl-piperazine and 0.83 ml (0.0060 mol) of triethylamine and the mixture was stirred at room temperature under argon for 3 hours The mixture was completely freed from the solvents and the residue was triturated in 5 ml of water. The resulting crystals were filtered off under suction, dried and chromatographed over silica gel with dichloromethane/methanol 19:1 as the eluent. 0.25 g of a yellowish solid was obtained.

b) The product was suspended in 5 ml of methanol and treated with excess hydrochloric acid in diethyl ether. Crystals separated from the resulting solution. The suspension was completely freed from the solvents and recrystallized from methanol/diethyl ether. 0.22 g (50%) of 2-methyl-5-(4-m-tolyl-piperazin-1-ylmethyl)-pyrimidin-4-ylamine hydrochloride (1:1.9) was obtained as white crystals; m.p. 263°–268°.

EXAMPLE 9

5-[4-(3-Methoxy-phenyl)-piperazin-1-ylmethyl]-2-methyl-pyrimidin-4-ylamine a) A suspension of 0.233 g (0.0012 mol) of 5-chloromethyl-2-methyl-pyrimidin-4-ylamine hydrochloride in 5 ml of dimethylformamide was treated with 0.477 g (0.0018 mol) of 1-(3-methoxy-phenyl)-piperazine dihydrochloride and 0.8 ml (0.006 mol) of triethylamine and the mixture was stirred at room temperature under argon for 1 hour. The mixture was completely freed from the solvents and the residue was triturated in 20 ml of water. The resulting crystals were filtered off under suction, dried and chromatographed over silica gel with dichloromethane/methanol 19:1 as the eluent. 0.33 g of a colourless solid was obtained.

b) The product was suspended in 5 ml of methanol and treated with excess hydrochloric acid in diethyl ether. Crystals separated from the resulting solution. The suspension was completely freed from the solvents and recrystallized from methanol. 0.23 g (50%) of 5-[4-(3-methoxy-phenyl)-piperazin-1-ylmethyl]-2-methyl-pyrimidin-4-ylamine dihydrochloride was obtained as white crystals; m.p. 262°–269°.

EXAMPLE 10

5-[4-(2-Chloro-phenyl)-piperazin-1-ylmethyl]-2-methyl-pyrimidin-4-ylamine a) A suspension of 0.19 g (0.001 2 mol) of 5-chloromethyl-2-methyl-pyrimidin-4-ylamine and 0.42 g (0.001 8 mol) of 1-(2-chloro-phenyl)-piperazine hydrochloride in 5 ml of dimethyl-formamide was treated with 0.56 ml (0.0040 mol) of triethylamine and the mixture was stirred at room temperature under argon for 2 hours. The mixture was completely freed from the solvents and the residue was triturated in 25 ml of water. The resulting crystals were filtered off under suction, dried and chromatographed over silica gel with dichloromethane/methanol 19:1 as the eluent. 0.18 g of a colourless solid was obtained.

b) The product was suspended in 3 ml of methanol and treated with excess hydrochloric acid in diethyl ether. Crystals separated from the resulting solution. The suspension was completely freed from the solvents and recrystallized from methanol/diethyl ether. 0.135 g (29%) of 5-[4-(2-chloro-phenyl)-piperazin-1-ylmethyl]-2-methyl-pyrimidin-4-ylamine dihydrochloride was obtained as white crystals; m.p. 284°–285°.

EXAMPLE 11

2-Methyl-5-(4-o-tolyl-piperazin-1-ylmethyl)-pyrimidin-4-ylamine a) A suspension of 7.7 g (0.040 mol) of 5-chloromethyl-2-methyl-pyrimidin-4-ylamine hydrochloride in 6 ml of dimethyl-formamide was treated with 15 g (0.11 mol) of dry potassium carbonate. At the same time a suspension of 10 g (0.040 mol) of 1-o-tolyl-piperazine dihydrochloride was treated with 15 g (0.11 mol) of dry potassium carbonate in 60 ml of dimethylformamide. After stirring at room temperature for ½ hr both solutions were combined and stirred for a further 4 hours. The reaction mixture was suction filtered, the residue was chromatographed over silica gel with dichloromethane/ethyl acetate 1:1 as the eluent and recrystallized from ethanol/ethyl acetate. 2.5 g of 2-methyl-5-(4-o-tolyl-piperazin-1-ylmethyl)-pyrimidin-4-ylamine were obtained as beige crystals; m.p. 189°–190°.

b) The product was dissolved in methanol and treated with excess hydrochloric acid in diethyl ether. Crystals separated from the resulting solution by the addition of diethyl ether. The crystals were filtered off under suction and dried in a vacuum. 2.7 g (18%) of 2-methyl-5-(4-o-tolyl-piperazin-1-ylmethyl)-pyrimidin-4-ylamine dihydrochloride were obtained as crystals; m.p. 312°–314°.

EXAMPLE 12

5-[4-(2-Methoxy-phenyl)-piperazin-1-ylmethyl]-2-methyl-pyrimidin-4-ylamine a) A suspension of 3.88 g (0.020 mol) of 5-chloromethyl-2-methyl-pyrimidin-4-ylamine hydrochloride, 3.84 g (0.020 mol) of (2-methoxy-phenyl)-piperazine, 6 g (0.043 mol) of dry potassium carbonate and 3.3 g (0.020 mol) of potassium iodide in 100 ml of dimethylformamide was dissolved at 80°. The reaction mixture was stirred at 80° for 2 hours and at 130° for 2 hours, cooled, suction filtered, completely freed from the solvents and digested in a small amount of diethyl ether. 2.4 g of an ochre coloured solid were obtained.

b) The product was dissolved in warm ethanol and treated with an excess of hydrochloric acid in diethyl ether. Crystals separated from the solution. ;2.4 g (31%) of 5-[4-(2-methoxy-phenyl)-piperazin- 1-ylmethyl]-2-methyl-pyrimidin-4-ylamine dihydrochloride were obtained as white crystals; m.p. 283°–284°.

EXAMPLE 13

2-Methyl-5-[4-(2-nitro-phenyl)-piperazin-1-ylmethyl]-pyrimidin-4-ylamine a) A solution of 1.25 g (0.0060 mol) of 1-(2-nitro-phenyl)-piperazine and 2.1 ml (0.015 mol) of triethylamine in 20 ml of dimethylformamide was treated with 0.97 g (0.0050 mol) of 5-chloromethyl-2-methyl-pyrimidin-4-ylamine hydrochloride and the mixture was stirred at room temperature under argon for 3 hours. The mixture was completely freed from the solvents and the residue was triturated in 20 ml of water. The resulting crystals were filtered off under suction, dried and chromatographed over silica gel with dichloromethane/methanol 19:1 as the eluent. 1.25 g (76%) of 2-methyl-5- [4-(2-nitro-phenyl )-piperazin-1-ylmethyl]-pyrimidin-4-ylamine were obtained as a yellow solid.

b) 0.27 g (0.00082 mol) of this product was suspended in 5 ml of methanol and treated with excess hydrochloric acid in diethyl ether. Crystals separated from the resulting solution. The suspension was completely freed from the solvents and recrystallized from methanol/diethyl ether. 0.28 g (85%) of 2-methyl-5-(4-(2-nitro-phenyl)-piperazin-1-ylmethyl]-pyrimidin-4-ylamine dihydrochloride was obtained as white crystals; m.p. 275°–280°.

EXAMPLE 14

5-(4-Phenyl-3,6-dihydro-2H-pyridin-1-ylmethyl)-2-methyl-pyrimidin-4-ylamine a) A suspension of 9.7 g (0.050 mol) of 5-chloromethyl-2-methyl-pyrimidin-4-ylamine hydrochloride, 9.8 g (0.050 mol) of 4-phenyl- 1,2,3,6-tetrahydropyridine hydrochloride and 13.8 g (0.1 00 mol) of dry potassium carbonate in 125 ml of dimethylformamide was stirred vigorously at 80° for 5 hours. The mixture was cooled, suction filtered, completely freed from the solvents and the residue was triturated in water. The resulting crystals were filtered off under suction and recrystallized from ethanol/water. 3.0 g (21%) of 5-(4-phenyl-3,6-dihydro-2H-pyridin-1-ylmethyl)-2-methyl-pyrimidin-4-ylamine were obtained as yellow crystals; m.p. 165°–166°.

b) The product was dissolved in ethanol and treated with excess hydrochloric acid in diethyl ether. Crystals separated from the solution. 3.8 g (100%) of 5-(4-phenyl-3,6-dihydro-2H-pyridin-1-ylmethyl)-2-methyl-pyrimidin-4-ylamine dihydrochloride were obtained as yellowish crystals; m.p. 266°–269°.

EXAMPLE 15

5-[4-(4-Fluoro-phenyl)-3,6-dihydro-2H-pyridin-1-ylmethyl]-2-methyl-pyrimidin-4-ylamine a) A suspension of 27.2 g (0.14 mol) of 5-chloromethyl-2-methyl-pyrimidin-4-ylamine hydrochloride, 29.8 g (0.14 mol) of 4-(4-fluoro-phenyl)-1,2,3,6-tetrahydropyridine hydrochloride and 42 g (0.30 mol) of dry potassium carbonate in 200 ml of dimethyl-formamide was stirred at room temperature for 18 hours. The mixture was suction filtered, the filter cake was washed with dichloromethane, the filtrate was completely freed from the solvents and the residue was crystallized twice from ethyl acetate/cyclohexane. 11.6 g (28%) of 5-[4-(4-fluoro-phenyl)-3,6-dihydro-2H-pyridin-1-ylmethyl]-2-methyl-pyrimidin-4-ylamine were obtained as yellowish crystals; m.p. 176°–178°.

b) 3.2 g (0.011 mol) of 5-[4-(4-fluoro-phenyl)-3,6-dihydro-2H-pyridin-1-ylmethyl]-2-methyl-pyrimidin-4-ylamine were dissolved in ethanol and treated with excess ethanolic hydrochloric acid. Crystals separated from the solution. 2.2 g (54%) of 5-[4-(4-fluoro-phenyl)-3,6-dihydro-2H-pyridin-1-ylmethyl]-2-methyl-pyrimidin-4-ylamine dihydrochloride were obtained as pale yellow crystals; m.p. 262°–264°.

EXAMPLE 16

5-[4-(4-Chloro-phenyl)-3,6-dihydro-2H-pyridin-1-ylmethyl]-methyl-pyrimidin-4-ylamine a) A suspension of 0.233 g (0.0012 mol) of 5-chloromethyl-2-methyl-pyrimidin-4-ylamine hydrochloride and 0.414 g (0.0018 mol of 4-(4-chloro-phenyl)-1,2,3,6-tetrahydropyridine hydrochloride in 5 ml of dimethylformamide was treated with 0.7 ml (0.0050 mol) of triethylamine and the mixture was stirred at room temperature under argon for 1 hour. The mixture was completely freed from the solvents and the residue was triturated in 25 ml of water. The resulting crystals were filtered off under suction, dried and chromatographed over silica gel with dichloromethane/methanol 19:1 as the eluent. 0.31 g of a colourless solid was obtained.

b) The product was suspended in 3 ml of methanol and treated with excess hydrochloric acid in diethyl ether. The suspension was completely freed from the solvents, recrystallized from methanol/diethyl ether and subsequently stirred under reflux in tert-butyl methyl ether for 1 hour, cooled, suction filtered and dried in a vacuum. 0.24 g (52%) of 5-[4-(4-chloro-phenyl)-3,6-dihydro-2H-pyridin-1-ylmethyl]-2-methyl-pyrimidin-4-ylamine dihydrochloride was obtained as white crystals; m.p. 265°–266°.

EXAMPLE 17

5-[4-(4-Methoxy-phenyl)-3,6-dihydro-2H-pyridin-1-ylmethyl]-2-methyl-pyrimidin-4-ylamine a) A suspension of 0.195 g (0.0010 mol) of 5-chloromethyl-2-methyl-pyrimidin-4-ylamine hydrochloride in 5 ml of dimethylformamide was treated with 0.56 ml (0.0040 mol) of triethylamine and 0.250 g (0.0011 mol) of 4-(4-methoxy-phenyl)-1,2,3,6-tetrahydropyridine hydrochloride and the mixture was stirred at room temperature under argon for 1 hour. The mixture was completely freed from the solvents and the residue was triturated in 5 ml of water. The resulting crystals were filtered off under suction, dried and chromatographed over silica gel with dichloromethane/methanol 19:1 as the eluent. 0.225 g of a colourless solid was obtained.

b) The product was suspended in 5 ml of methanol and treated with excess hydrochloric acid in diethyl ether. Crystals separated from the resulting solution. The suspension was completely freed from the solvents and recrystallized from methanol. 0.19 g (50%) of 5-[4-(4-methoxy-phenyl)-3,6-dihydro-2H-pyridin-1-ylmethyl]-2-methyl-pyrimidin-4-ylamine dihydrochloride was obtained as white crystals; m.p. 254°–256°.

EXAMPLE 18

5-(3,4-Dihydro-1H-isoquinolin-2-methyl-pyrimidin-4-ylamine a) A suspension of 0.80 g (0.0041 2 mol) of 5-chloromethyl-2-methyl-pyrimidin-4-ylamine hydrochloride in 17 ml of dimethylformamide was treated with 1.7 ml (0.0123 mol) of triethylamine and 0.67 g (5.3 mol) of 1,2,3,4-tetrahydroisoquinoline and the mixture was stirred at room temperature under argon for 3 hours. The mixture was completely freed from the solvents and the residue was chromatographed over silica gel with dichloromethane/methanol 9:1 as the eluent and recrystallized from ethyl acetate/diethyl ether. 0.72 g (69%) of 5-(3,4-dihydro-1H-isoquinolin-2-ylmethyl)-2-methyl-pyrimidin-4-ylamine was obtained as beige crystals; m.p. 150°–153°.

b) A solution of 0.70 g (0.00275 mol) of 5-(3,4-dihydro-1H-isoquinolin-2-ylmethyl)-2-methyl-pyrimidin-4-ylamine in 15 ml of methanol was treated with 0.85 ml (0.00435 mol) of 3.5N ethanolic hydrochloric acid. The solution was completely freed from the solvents and the residue was recrystallized from methanol. 0.29 g (32%) of 5-(3,4-dihydro-1H-isoquinolin-2-ylmethyl)-2-methyl-pyrimidin-4-ylamine dihydrochloride was obtained as white crystals; m.p. 260°–265°.

EXAMPLE 19

2-Methyl-5-(6-phenyl-3,4-dihydro-1H-isoquinolin-2-ylmethyl)-pyrimidin-4-ylamine a) A suspension of 0.20 g (0.00080 mol) of 5-chloromethyl-2-methyl-pyrimidin-4-ylamine hydrochloride in 10 ml of dimethylformamide was treated with 0.34 ml (0.0024 mol) of triethylamine and 0.19 g (0.00097 mol) of 6-phenyl-1,2,3,4-tetrahydro-isoquinoline and the mixture was stirred at room temperature under argon for 60 hours The mixture was completely freed from the solvents. The residue was partitioned between dichloromethane and water, extracted, chromatographed over silica gel with acetonitrile/methanol 5:1 as the eluent and digested in diethyl ether. 0.16 g (61%) of 2-methyl-5-(6-phenyl-3,4-dihydro-1H-isoquinolin-2-ylmethyl)-pyrimidin-4-ylamine was obtained as white crystals; m.p. 186°–188°. A further 0.03 g of pale yellow crystals was recovered from the mother liquor.

b) A solution of 0.177 g (0.00053 mol) of 2-methyl-5-(6-phenyl-3,4-dihydro-1H-isoquinolin-2-ylmethyl )-pyrimidin-4-ylamine in 20 ml of ethanol was treated with 0.15 ml (0.000525 mol) of 3.5N ethanolic hydrochloric acid. The solution was completely freed from the solvents and the residue was recrystallized from ethanol/diethyl ether. 0.10 g (47%) of 2-methyl-5-(6-phenyl-3,4-dihydro-1H-isoquinolin-2-ylmethyl)-pyrimidin-4-ylamine dihydrochloride was obtained as white crystals; m.p. 212°–214°.

EXAMPLE 20

5-(6-Methoxy-3,4-dihydro-1H-isoquinolin-2-ylmethyl)-2-methyl-pyrimidin-4-ylamine A suspension of 0.80 g (0.00412 mol) of 5-chloromethyl-2-methyl-pyrimidin-4-ylamine hydrochloride in 17 ml of dimethylformamide was treated with 1.7 ml (0.0124 mol) of triethylamine and 0.87 g (0.0053 mol) of 6-methoxy-1,2,3,4-tetrahydro-isoquinoline and the mixture was stirred at room temperature under argon for 3 hours. The mixture was completely freed from the solvents and the residue was triturated in 20 ml of water. The resulting crystals were filtered off under suction, chromatographed over silica gel with dichloromethane/methanol 9:1 as the eluent and recrystallized from ethyl acetate/n-hexane. 0.26 g (22%) of 5-(6-methoxy-3,4-dihydro-1H-isoquinolin-2-ylmethyl)-2-methyl-pyrimidin-4-ylamine was obtained as white crystals; m.p. 142°–143°.

EXAMPLE 21

2-Methyl-5-(7-phenyl-3,4-dihydro-1H-isoquinolin-2-ylmethyl)-pyrimidin-4-ylamine a) A suspension of 0.17 g (0.00088 mol) of 5-chloromethyl-2-methyl-pyrimidin-4-ylamine in 10 ml of dimethylformamide was treated with 0.30 ml (0.0021 mol) of triethylamine and 0.184 g (0.00088 mol) of 7-phenyl-1,2,3,4-tetrahydro-isoquinoline and the mixture was stirred at room temperature under argon for 18 hours. The solvent was distilled off in a high vacuum. The residue was partitioned between dichloromethane/water, extracted and dried over MgSO$_4$. After removing the solvent the residue was chromatographed over silica gel with ethyl acetate as the eluent. 0.22 g (76%) of 2-methyl-5-(7-phenyl-3,4-dihydro-1H-isoquinolin-2-ylmethyl)-pyrimidin-4-ylamine was obtained as a light yellowish solid; m.p. 147°–149°.

b) 0.213 g (0.00064 mol) of 2-methyl-5-(7-phenyl-3,4-dihydro-1H-isoquinolin-2-ylmethyl)-pyrimidin-4-ylamine was suspended in 2 ml of methanol and treated with 10 ml of 2.1M methanolic HCl, with a colourless precipitate separating. After suction filtration, washing and drying in a high vacuum 0.15 g (58%) of 2-methyl-5-(7-phenyl-3,4-dihydro-1H-isoquinolin-2-ylmethyl)-pyrimidin-4-ylamine dihydrochloride was obtained as colourless crystals; m.p. 290° (dec.).

EXAMPLE 22

5-(7-Benzyloxy-3,4-dihydro-1H-isoquinolin-2-ylmethyl-2-methyl-pyrimidin-4-ylamine a) A suspension of 0.23 g (0.0012 mol) of 5-chloromethyl-2-methyl-pyrimidin-4-ylamine in 10 ml of dimethylformamide was treated with 0.42 ml (0.0030 mol) of triethylamine and 0.29 g (0.0012 mol) of 7-benzyloxy-1,2,3,4-tetrahydro-isoquinoline and the mixture was stirred at room temperature under argon for 18 hours. The solvent was distilled off in a high vacuum. The residue was partitioned between dichloromethane/water, extracted and dried over MgSO$_4$.

After removing the solvent the residue was chromatographed on silica gel with ethyl acetate as the eluent. 0.22 g (51%) of 5-(7-benzyloxy-3,4-dihydro-1H-isoquinolin-2-ylmethyl)- 2-methyl-pyrimidin-4-ylamine was obtained as a colourless solid; m.p. 151°–153°.

b) 0.22 g (0.00061 mol) of 5-(7-benzyloxy-3,4-dihydro-1H-isoquinolin-2-ylmethyl)-2-methyl-pyrimidin-4-ylamine was suspended in 2 ml of methanol and treated with 10 ml of 2.1M methanolic HCl, with a colourless precipitate separating. After suction filtration, washing and drying in a high vacuum 0.25 g (96%) of 5-(7-benzyloxy-3,4-dihydro-1H-isoquinolin-2-ylmethyl)-pyrimidin-4-ylamine dihydrochloride was obtained as colourless crystals; m.p. 290° (dec.).

EXAMPLE 23

5-(5-Benzyloxy-3,4-dihydro-1H-isoquinolin-2-ylmethyl)-2-methyl-pyrimidin-4-ylamine a) A suspension of 0.098 g (0.00051 mol) of 5-chloromethyl-2-methyl-pyrimidin-4-ylamine in 2 ml of dimethylformamide was treated with 0.21 ml (0.0015 mol) of triethylamine and 0.145 g (0.00061 mol) of 5-benzyloxy-1,2,3,4-tetrahydro-isoquinoline (WO 94/20459) and the mixture was stirred at room temperature under argon for 18 hours The solvent was distilled off in a high vacuum. The residue was partitioned between dichloro-methane/water, extracted and dried over MgSO$_4$. After removing the solvent the residue was chromatographed on silica gel with ethyl acetate as the eluent. 0.153 g (84%) of 5-(5-benzyloxy-3,4-dihydro-1H-isoquinolin-2-ylmethyl)-2-methyl-pyrimidin-4-ylamine was obtained as a yellowish oil. MS (ISP): me/e= 361 ($C_{22}H_{25}N_4O^+$).

b) 0.15 g (0.00042 mol) of 5-(5-benzyloxy-3,4-dihydro-1H-isoquinolin-2-ylmethyl)-2-methyl-pyrimidin-4-ylamine was suspended in 8 ml of methanol and treated with 4 ml of 2.1M methanolic HCl. After 20 minutes diethyl ether was added thereto, with a colourless precipitate separating. After suction filtration, washing and drying in a high vacuum 0.13 g (71%) of 5-(5-benzyloxy- 3,4-dihydro-1H-isoquinolin-2-ylmethyl)-pyrimidin-4-ylamine dihydrochloride was obtained as beige crystals; m.p. 273°–275° (dec.).

EXAMPLE 24

5-(3,4,5,6,7,8-Hexahydro-1H-isoquinolin-2-ylmethyl)-2-methyl-pyrimidin-4-ylamine a) A suspension of 11.6 g (0.060 mol) of 5-chloromethyl-2-methyl-pyrimidin-4-ylamine hydrochloride in 40 ml of dimethyl-formamide was treated with 8.0 ml (0.060 mol) of 5,6,7,8-tetra-hydro-isoquinoline, dissolved at 120° and stirred at 800 for 16 hours. The mixture was cooled, suction filtered, washed with a small amount of dimethylformamide, then with ethyl acetate and dried in a vacuum. 16.5 g (84%) of 2-(4-amino-2-methyl-pyrimidin-5-ylmethyl)-5,6,7,8-tetrahydro-isoquinolinium chloride hydrochloride were obtained as yellowish crystals; m.p. 242°–244°.

b) A solution of 9.81 g (0.030 mol) of 2-(4-amino-2-methyl-pyrimidin-5-ylmethyl)-5,6,7,8-tetrahydro-isoquinolinium chloride hydrochloride in 50 ml of methanol was treated portionwise at 10° with 3.5 g (0.092 mol) of sodium borohydride. The mixture was stirred at room temperature for 1 hour and completely freed from the solvents. The residue was partitioned between ethyl acetate and water, extracted and recrystallized from petroleum ether. 5.7 g (74%) of 5-(3,4,5,6,7,8-hexahydro-1H-isoquinolin-2-ylmethyl)-2-methyl-pyrimidin-4-ylamine were obtained as white crystals; m.p. 137°–139° (dec.).

c) A solution of 1.74 g (0.00673 mol) of 5-(3,4,5,6,7,8-hexahydro-1H-isoquinolin-2-ylmethyl)-2-methyl-pyrimidin-4-ylamine in 40 ml of ethanol was treated with 3.85 ml (0.0135 mol) of 3.5N ethanolic hydrochloric acid. The solution was completely freed from the solvents and the residue was recrystallized from methanol/diethyl ether. 2.16 g (97%) of 5-(3,4,5,6,7,8-hexahydro- 1H-isoquinolin-2-ylmethyl)-2-methyl-pyrimidin-4-ylamine dihydrochloride were obtained as white crystals; m.p. 248°–250°.

EXAMPLE 25

5-(4-Ethyl-3,6-dihydro-2H-pyridin-1-ylmethyl)-2-methyl-pyrimidin-4-ylamine a) A suspension of 0.95 g (0.0050 mol) of 5-chloromethyl-2-methyl-pyrimidin-4-ylamine in 13 ml of dimethylformamide was treated with 3.5 ml (0.025 mol) of triethylamine and 1.16 g (0.010) of 4-ethyl-1,2,3,6-tetrahydropyridine and the mixture was stirred at room temperature under argon for 18 hours. The solvent was distilled off in a high vacuum. The residue was partitioned between dichloromethane/water, extracted and dried over MgSO$_4$. After removing the solvent the residue was chromatographed on silica gel with ethyl acetate as the eluent. 0.60 g (52%) of 5-(4-ethyl-3,6-dihydro-2H-pyridin-1-ylmethyl)-2-methyl-pyrimidin-4-ylamine were obtained as a beige solid; m.p. 75°–76°.

b) 0.16 g (0.00069 mol) of 5-(4-ethyl-3,6-dihydro-2H-pyridin-1-ylmethyl)-2-methyl-pyrimidin-4-ylamine was dissolved in 2 ml of ethanol and treated with 1 ml of 2.4M ethereal HCl. The mixture was diluted with 5 ml of diethyl ether, with a colourless precipitate separating. After suction filtration, washing and drying in a high vacuum 0.18 g (84%) of 5-(4-ethyl-3,6-dihydro-2H-pyridin-1-ylmethyl)-2-methyl-pyrimidin-4-ylamine dihydrochloride was obtained as colourless crystals; m.p. >245° (dec.).

EXAMPLE 26

1-(4-Amino-2-methyl-pyrimidin-5-ylmethyl)-1,2,3,6-tetrahydro-pyridin-4-ylmethyl benzoate a) A suspension of 0.195 g (0.0010 mol) of 5-chloromethyl-2-methyl-pyrimidin-4-ylamine in 5 ml of dimethylformamide was treated with 0.42 ml (0.0030 mol) of triethylamine and 0.365 g (0.0010 mol) of 1,2,3,4-tetrahydro-pyridin-4-ylmethyl benzoate and the mixture was stirred at room temperature under argon for 18 hours. The solvent was distilled off in a high vacuum. The residue was partitioned between dichloromethane/water, extracted and dried over MgSO$_4$. After removing the solvent the residue was chromatographed over silica gel with ethyl acetate as the eluent. 0.17 g (74%) of 1-(4-amino-2-methyl-pyrimidin-5-ylmethyl)-1,2,3,6-tetrahydro-pyridin-4-ylmethyl benzoate was obtained as a yellow oil. MS (ISP): me/e=339 ($C_{19}H_{23}N_4O_2^+$).

b) 0.16 g (0.00050 mol) of 1-(4-amino-2-methyl-pyrimidin-5-ylmethyl)-1,2,3,6-tetrahydro-pyridin-4-ylmethyl benzoate was dissolved in 2 ml of methanol and treated with 2.5 ml of 2.1M methanolic HCl. A colourless precipitate separated. After suction filtration, washing and drying in a high vacuum 0.125 g (61%) of 1-(4-amino-2-methyl-pyrimidin-5-ylmethyl)-1,2,3,6-tetrahydro-pyridin-4-ylmethyl benzoate dihydrochloride was obtained as colourless crystals; m.p. >265° (dec.).

EXAMPLE 27

[5-(4-Benzyloxymethyl-3,6-dihydro-2H-pyridin-1-ylmethyl)-2-methyl-pyrimidin-4-yl]-amine a) 10.7 ml (0.0901 mol) of benzyl bromide were added to a solution of 8.9 g (0.0815 mol) of 4-hydroxymethylpyridine in 30 ml of dimethylformamide and the mixture was stirred at 100° for 2 hours. Subsequently, the reaction mixture was cooled to room temperature, diluted with 111 ml of ethanol and treated portion-wise with 3.9 g (0.103 mol) of NaBH$_4$. The mixture was boiled under reflux for 3 hours and stirred at room temperature for a further 18 hours. Then, the solvent was distilled off, the residue was partitioned between dichloromethane/water, extracted and dried. After removal of the solvent the residue was chromatographed on silica gel with ethyl acetate/hexane 1:1 as the eluent. 9.26 g (56%) of (1-benzyl-1,2,3,6-tetrahydro-pyridin-4-yl)-methanol were obtained as yellow crystals; m.p. 57°–60°.

b) 1.016 g (0.0050 mol) of (1-benzyl-1,2,3,6-tetrahydro-pyridin-4-yl)-methanol were added to a suspension of 0.20 g (0.0050 mol) of NaH (60% in oil) in 10 ml of tetrahydrofuran and the mixture was stirred at room temperature for 30 minutes Then, 0.60 ml (0.0050 mol) of benzyl bromide was added and the mixture was stirred at room temperature for a further 2 hours. The reaction mixture was subsequently treated with water and extracted with diethyl ether. The organic phase was dried over MgSO$_4$, concentrated and the residue was chromatographed on silica gel with hexane/ethyl acetate 9:1 to 3:1 as the eluent. 0.515 g (35%) of 1-benzyl-4-benzyloxymethyl-1,2,3,6-tetrahydropyridine was obtained as a yellow oil. MS (ISP): me/e=2.94 (C$_{20}$H$_{24}$NO$^+$).

c) 0.24 ml (0.0022 mol) of 1-chloroethyl chloroformate was added to a solution of 0.495 g (0.00169 mol) of 1-benzyl-4-benzyloxymethyl-1,2,3,6-tetrahydropyridine in 19 ml of dichloro-methane while cooling with ice and the mixture was stirred at 0° for 1.5 hours. Thereafter, the mixture was concentrated and the residue was treated with 19 ml of methanol. The mixture was boiled at reflux for 2 hours, again concentrated and the residue was partitioned between ethyl acetate/water, extracted and dried over Na$_2$SO$_4$. After concentration and drying in a high vacuum 0.376 g of 4-benzyloxymethyl-1,2,3,6-tetrahydro-pyridine was obtained as a brown oil which was contaminated with 30% of starting material (65%). MS (ISP): me/e=204 (C$_{13}$H$_{18}$NO$^+$).

d) A suspension of 0.327 g (0.001 68 mol) of 5-chloromethyl-2-methyl-pyrimidin-4-ylamine in 8 ml of dimethylformamide was treated with 0.7 ml (0.0050 mol) of triethylamine and 0.37 g (0.00168 mol) of 4-benzyloxymethyl-1,2,3,6-tetrahydro-pyridine (contaminated with 30% of 1-benzyl-4-benzyloxymethyl-1, 2,3,6-tetrahydro-pyridine) and the mixture was stirred at room temperature under argon for 18 hours. The solvent was distilled off in a high vacuum. The residue was partitioned between dichloromethane/water, extracted and dried over MgSO$_4$. After removing the solvent the residue was chromatographed on silica gel with ethyl acetate as the eluent. 0.19 g (53%) of [5-(4-benzyloxy-methyl-3,6-dihydro-2H-pyridin-1-ylmethyl)-2-methyl-pyrimidin-4-yl]-amine was obtained as a yellow oil. MS (ISP): me/e=325 (C$_{19}$H$_{25}$N$_4$O$^+$).

e) 0.185 g (0.00057 mol) of [5-(4-benzyloxymethyl-3,6-dihydro-2H-pyridin-1-ylmethyl)-2-methyl-pyrimidin-4-yl]-amine was dissolved in 3 ml of methanol and treated with 27 ml of 2.1M methanolic HCl. A colourless precipitate separated. After suction filtration, washing and drying in a high vacuum 0.075 g (33%) of [5-(4-benzyloxymethyl-3,6-dihydro-2H-pyridin-1-ylmethyl)-2-methyl-pyrimidin-4-yl]-amine dihydrochloride was obtained as colourless crystals; m.p. >244° (dec.).

EXAMPLE 28

2-Methyl-5-(4-phenethyl-3,6-dihydro-2H-pyridin-1-ylmethyl)-pyrimidin-4-ylamine a) A warm solution of 0.5 g (0.0026 mol) of 5-chloromethyl-2-methyl-pyrimidin-4-ylamine hydrochloride in 40 ml of dimethylformamide was treated with 0.4 g (0.0021 mol) of 4-phenethyl-1,2,3,6-tetrahydro-pyridine and 0.9 ml (0.0064 mol) of triethylamine and the mixture was stirred at room temperature for 24 hours. The mixture was completely freed from the solvents. The residue was partitioned between dichloromethane and water, extracted, chromatographed over silica gel with acetonitrile/ethanol 8:1 as the eluent and digested in diethyl ether. 0.18 g (22%) of 2-methyl-5-(4-phenethyl-3,6-dihydro-2H-pyridin-1-ylmethyl)-pyrimidin-4-ylamine was obtained as white crystals; m.p. 152°–154°. A further 0.03 g of yellowish crystals was recovered from the mother liquor.

b) A solution of 0.177 g (0.00057 mol) of 2-methyl-5-(4-phenethyl-3,6-dihydro-2H-pyridin-1-ylmethyl)-pyrimidin-4-ylamine in 10 ml of ethanol was treated with 0.16 ml (0.00057 mol) of 3.5N ethanolic hydrochloric acid. The solution was completely freed from the solvents and the residue was recrystallized from methanol/diethyl ether. 0.110 g (51%) of 2-methyl-5-(4-phenethyl-3,6-dihydro-2H-pyridin-1-ylmethyl)-pyrimidin-4-ylamine dihydrochloride was obtained as white crystals; m.p. 235°–237°.

EXAMPLE 29

(E)-2-Methyl-5-(4-styryl-3,6-dihydro-2H-pyridin-1-ylmethyl)-pyrimidin-4-ylamine a) A suspension of 0.08 g (0.00045 mol) of 5-chloromethyl-2-methyl-pyrimidin-4-ylamine hydrochloride in 5 ml of dimethylformamide was treated with 0.085 g (0.000545 mol) of (E)-4-stylryl-1,2,3,6-tetrahydro-pyridine and the mixture was stirred at room temperature under argon for 55 hours. The mixture was completely freed from the solvents. The residue was partitioned between dichloromethane and water, extracted, chromatographed over silica gel with acetonitrile/methanol 5:1 as the eluent and recrystallized from ethanol. 0.078 g (61%) of (E)-2-methyl-5-(4-styryl-3,6-dihydro-2H-pyridin-1-ylmethyl)-pyrimidin-4-ylamine was obtained as white crystals; m.p. 199°–203°.

b) A solution of 0.077 g (0.00025 mol) of (E)-2-methyl-5-(4-styryl-3,6-dihydro-2H-pyridin-1-ylmethyl)-pyrimidin-4-ylamine in 30 ml of methanol/dichloromethane 1:1 was treated with 0.07 ml (0.00026 mol) of 3.5N ethanolic hydrochloric acid. The solution was completely freed from the solvents and recrystallized from ethanol/diethyl ether. 0.046 g (54%) of (E)-2-methyl-5-(4-styryl-3,6-dihydro-2H-pyridin-1-ylmethyl)-pyrimidin-4-ylamine hydrochloride (1:1.2) was obtained as yellowish crystals; m.p. 185°–192°.

EXAMPLE 30

2-Methyl-5-(4-phenylethynyl-3,6-dihydro-2H-pyridin-1-ylmethyl)-pyrimidin-4-ylamine A solution of 0.19 g (0.00098 mol) of 5-chloromethyl-2-methyl-pyrimidin-4-ylamine hydrochloride in 20 ml of dimethyl-formamide was treated with 0.15 g (0.82 mol) of 4-phenylethynyl-1,2,3,4-tetrahydro-pyridine and 0.34 ml (0.0024 mol) of triethylamine and the mixture was stirred at room temperature under argon for 16 hours. The mixture was completely freed from the solvents. The residue was partitioned between dichloromethane and water, extracted, chromatographed over silica gel with acetonitrile/ethanol 8:1 as the eluent and digested in diethyl ether. 0.10 g (34%) of 2-methyl-5-(4-phenylethynyl-3,6-dihydro-2H-pyridin-1-ylmethyl)-pyrimidin-4-ylamine as white crystals; m.p. 187°–188°.

EXAMPLE 31

2-Methyl-5-(4-phenethyl-piperazin-1-ylmethyl)-pyrimidin-4-ylamine a) A suspension of 0.30 g (0.0019 mol) of 5-chloromethyl-2-methyl-pyrimidin-4-ylamine hydrochloride in 20 ml of dimethylformamide was treated with 0.30 g (0.00157 mol) of 1-phenethyl-piperazine and 0.66 ml (0.0047 mol) of triethylamine and the mixture was stirred at room temperature under argon for 36 hours. The mixture was completely freed from the solvents. The residue was partitioned between dichloromethane and water, extracted, chromatographed over silica gel with methanol as the eluent and recrystallized from toluene. 0.39 g (83%) of 2-methyl-5-(4-phenethyl-piperazin-1-ylmethyl)-pyrimidin-4-ylamine was obtained as white crystals; m.p. 162°–165°.

b) A solution of 0.37 g (0.0012 mol) of 2-methyl-5-(4-phenethyl-piperazin-1-ylmethyl)-pyrimidin-4-ylamine in 20 ml of methanol was treated with 0.37 ml (0.00129 mol) of 3.5N ethanolic hydrochloric acid, The solution was completely freed from the solvents and the residue was recrystallized from ethanol. 0.36 g (87%) of 2-methyl-5-(4-phenethyl-piperazin-1-ylmethyl)-pyrimidin-4-ylamine hydrochloride (1:1.2) was obtained as white crystals; m.p. 240°–242°.

EXAMPLE 32

[5-(4-Benzyloxymethyl-piperidin-1-ylmethyl )-2-methyl-pyrimidin-4-yl]-amine a) A suspension of 0.040 g of platinum dioxide in 2 ml of tetrahydrofuran was treated with a solution of 0.11 g (0.00034 mol) of [5-(4-benzyloxymethyl-3,6-dihydro-2H-pyridin-1-ylmethyl)-2-methyl-pyrimidin-4-yl]-amine in 3.5 ml of tetrahydrofuran and the mixture was hydrogenated under normal pressure for 5 hours. The catalyst was filtered off, the filtrate was concentrated and the residue was chromatographed on silica gel with ethyl acetate as the eluent. 0.078 g (70%) of [5-(4-benzyloxymethyl-piperidin-1-ylmethyl)-2-methyl-pyrimidin-4-yl]-amine was obtained as colourless crystals; m.p. 106°–108°.

b) 0.076 g (0.000233 mol) of [5-(4-benzyloxymethyl-piperidin-1-ylmethyl)-2-methyl-pyrimidin-4-yl]-amine was dissolved in 1.2 ml of methanol and treated with 1.1 ml of 2.1M methanolic HCl. After adding some diethyl ether a colourless precipitate separated. This was filtered off under suction, washed and dried in a high vacuum. 0.044 g (47%) of [5-(4-benzyloxymethyl-piperidin-1-ylmethyl)-2-methyl-pyrimidin-4-yl]-amine dihydrochloride was obtained as colourless crystals; m.p. >247° (dec.).

EXAMPLE 33

5- [4-(2-Methoxy-phenyl)-piperazin-1-ylmethyl]-2-propyl-pyrimidin-4-ylamine a) A suspension of 7.0 g (0.020 mol) of 5-bromomethyl-2-propyl-pyrimidin-4-ylamine dihydrobromide, 3.85 g (0.020 mol) of (2-methoxy-phenyl)-piperazine and 6 g (0.043 mol) of dry potassium carbonate in 75 ml of dimethylformamide was dissolved at room temperature for 4 hours. The reaction mixture was suction filtered, the filter cake was washed with ethyl acetate and ethanol, the filtrate was completely freed from the solvents and the residue was chromatographed over silica gel with ethyl acetate as the eluent and recrystallized from hot ethyl acetate. 1.3 g (21%) of 5-[4-(2-methoxy-phenyl)-piperazin-1-ylmethyl]-2-propyl-pyrimidin-4-ylamine were obtained as yellowish crystals, m.p. 130°.

b) The product was dissolved in warm ethanol and treated with excess hydrochloric acid in diethyl ether. Crystals separated from the solution. 1.3 g (81%) of 5-[4-(2-methoxy-phenyl)-piperazin-1-ylmethyl]-2-propyl-pyrimidin-4-ylamine dihydrochloride were obtained as yellowish crystals; m.p. 281°.

EXAMPLE 34

5-[4-(4-Fluoro-phenyl )-3,6-dihydro-2H-pyridin-1-ylmethyl]-2-propyl-pyrimidin-4-ylamine a) A suspension of 7.0 g (0.020 mol) of 5-bromomethyl-2-propyl-pyrimidin-4-ylamine dihydrobromide, 4.2 g (0.020 mol) of 4-(4-fluoro-phenyl)-1,2,3,6-tetrahydropyridine hydrochloride and 8.0 g (0.060 mol) of dry potassium carbonate in 60 ml of dimethylformamide was stirred at room temperature for 18 hours. The mixture was suction filtered, the filter cake was washed with dichloromethane, the filtrate was completely freed from the solvents and the residue was recrystallized twice from ethyl acetate/cyclohexane and then from hot ethanol. 1.4 g (21%) of 5-[4-(4-fluoro-phenyl)-3,6-dihydro-2H-pyridin-1-ylmethyl]-2-propyl-pyrimidin-4-ylamine were obtained as white crystals; m.p. 142°–145°.

b) The product (0.00429 mol) was dissolved in warm ethanol and treated with excess hydrochloric acid in diethyl ether. Crystals separated from the solution. 1.0 g (58%) of 5-[4-(4-fluoro-phenyl)-3,6-dihydro-2H-pyridin-1-ylmethyl]-2-propyl-pyrimidin-4-ylamine dihydrochloride was obtained as pale yellowish crystals; m.p. 265°–266°.

EXAMPLE 35

5-(4-Phenyl-piperazin-1-ylmethyl)-pyrimidine-2,4-diamine a) A solution of 0.14 g (0.00086 mol) of 1-phenyl-piperazine in 10 ml of tetrahydrofuran was treated with 0.6 ml (0.0043 mol) of triethylamine and 0.24 g (0.00086 mol) of 5-bromomethyl-pyrimidine-2,4-diamine dihydrobromide and the mixture was stirred at room temperature under argon for 16 hours. The suspension obtained was suction filtered and the filtrate was completely freed from the solvents. The residue was chromatographed over silica gel with acetonitrile/methanol 1:1 as the eluent and digested in diethyl ether. 0.14 g (57%) of 5-(4-phenyl-piperazin-1-ylmethyl)-pyrimidine-2,4-diamine was obtained as white crystals; m.p. 263°–265°. A further 0.04 g of yellowish crystals was recovered from the mother liquor.

b) 0.17 g (0.00059 mol) of 5-(4-phenyl-piperazin-1-ylmethyl)-pyrimidine-2,4-diamine was dissolved in 120 ml of hot methanol. The solution was treated at room temperature with 0.32 ml (0.00118 mol) of 3.7N ethanolic hydrochloric acid. The solution was completely freed from the solvents and the residue was recrystallized from methanol/diethyl ether. 0.21 g (71%) of 5-(4-phenyl-piperazin-1-ylmethyl)-pyrimidine-2,4-diamine dihydrochloride was obtained as white crystals; m.p. 275°–277°.

EXAMPLE 36

5-[4-(4-Chloro-phenyl)-piperazin-1-ylmethyl]-pyrimidine-2,4-diamine a) A solution of 0.97 g (0.00493 mol) of 1-(4-chloro-phenyl)-piperazine in 35 ml of dimethylformamide was treated with 1.37 ml (0.00986 mol) of triethylamine and 0.60 g (0.0016 mol) of 5-bromomethyl-pyrimidine-2,4-diamine dihydrobromide and the mixture was stirred at room temperature under argon for 60 hours. The mixture was completely freed from the solvents. The residue was chromatographed over silica gel with acetonitrile/methanol 1:1 as the eluent, digested in dichloromethane/water 1:1 and subsequently filtered off under suction. 0.21 g (40%) of 5-[4-(4-chloro-phenyl)-piperazin-1-ylmethyl]-pyrimidine-2,4-diamine was obtained as white crystals; m.p. 296°–298°.

b) 0.18 g (0.00056 mol) of 5-[4-(4-chloro-phenyl)-piperazin-1-ylmethyl]-pyrimidine-2,4-diamine was dissolved in 250 ml of hot methanol. The solution was treated at room temperature with 0.32 ml (0.00112 mol) of 3.5N ethanolic hydrochloric acid. The solution was completely freed from the solvents and the residue was recrystallized from methanol/diethyl ether. 0.22 g (100%) of 5-[4-(4-chloro-phenyl)-piperazin-1-ylmethyl]-pyrimidine-2,4-diamine hydrochloride (1:1.9) was obtained as white crystals; m.p. 252°–253°.

EXAMPLE 37

5-(4-p-Tolyl-piperazin-1-ylmethyl)-pyrimidine-2,4-diamine a) A solution of 0.87 g (0.00493 mol) of 1-p-tolyl-piperazine in 30 ml of dimethylformamide was treated with 1.37 ml (0.00986 mol) of triethylamine and 0.60 g (0.00164 mol) of 5-bromomethyl-pyrimidine- 2,4-diamine dihydrobromide and the mixture was stirred at room temperature under argon for 110 hours. The mixture was completely freed from the solvents. The residue was chromatographed over silica gel with methanol as the eluent, digested in dichloromethane/water 1:1 and subsequently filtered off under suction. 0.25 g (51%) of 5-(4-p-tolyl-piperazin-1-ylmethyl)-pyrimidine-2,4-diamine was obtained as beige crystals; m.p. 248°–250°.

b) 0.23 g (0.00077 mol) of 5-(4-p-tolyl-piperazin-1-ylmethyl)-pyrimidine-2,4-diamine was dissolved in 220 ml of hot methanol. The solution was treated at room temperature with 0.44 ml (0.00154 mol) of 3.5N ethanolic hydrochloric acid. The solution was completely freed from the solvents and the residue was recrystallized from ethanol/diethyl ether. 0.22 g (77%) of 5-(4-p-tolyl-piperazin-1-ylmethyl)-pyrimidine-2,4-diamine dihydrochloride was obtained as whited crystals; m.p. 220°–222°.

EXAMPLE 38

5-[4-(4-Methoxy-phenyl)-piperazin-1-ylmethyl]-pyrimidine-2,4-diamine a) A solution of 0.95 g (0.00494 mol) of 1-(4-methoxy-phenyl)-piperazine in 30 ml of dimethylformamide was treated with 1.37 ml (0.00986 mol) of triethylamine and 0.60 g (0.00164 mol) of 5-bromomethyl-pyrimidine-2,4-diamine dihydrobromide and the mixture was stirred at room temperature under argon for 65 hours. The mixture was completely freed from the solvents. The residue was chromatographed over silica gel with acetonitrile/methanol (1:1 ), digested in diethyl ether and subsequently filtered off under suction. 0.24 g (47%) of 5-[4-(4-methoxy-phenyl)-piperazin-1-ylmethyl]-pyrimidine-2,4-diamine was obtained as white crystals; m.p. 239°–241°.

b) 0.23 g (0.00073 mol) of 5-[4-(4-methoxy-phenyl)-piperazin-1-ylmethyl]-pyrimidine-2,4-diamine was dissolved in 250 ml of hot methanol. The solution was treated at room temperature with 0.84 ml (0.00293 mol) of 3.5N ethanolic hydrochloric acid. The solution was completely freed from the solvents and recrystallized from methanol/diethyl ether. 0.27 g (96%) of 5-[4-(4-methoxy-phenyl)-piperazin-1-ylmethyl]-pyrimidine-2,4-diamine hydrochloride (1:2.3) was obtained as white crystals; m.p. 215°–216°.

EXAMPLE 39

5- [4-(3-Chloro-phenyl)-piperazin-1-ylmethyl]-pyrimidine-2,4-diamine

A solution of 13.5 g (0.050 mol) of 1-(3-chloro-phenyl)-piperazine in 500 ml of tetrahydrofuran was treated with 35 ml (0.25 mol) of triethylamine and 18.2 g (0.050 mol) of 5-bromomethyl-pyrimidine-2,4-diamine dihydrobromide and the mixture was stirred at room temperature under argon for 16 hours. The suspension obtained was suction filtered and the filtrate was completely freed from the solvents. The residue was chromatographed over silica gel with acetonitrile/methanol 1:1 as the eluent and digested in diethyl ether. 10 g (63%) of 5-[4-(3-chloro-phenyl)-piperazin-1-ylmethyl]-pyrimidine-2,4-diamine were obtained as beige crystals; m.p. 222°–226°.

EXAMPLE 40

5-[4-(2-Chloro-phenyl)-piperazin-1-ylmethyl]-pyrimidine-2,4-diamine

A solution of 8.0 g (0.031 mol) of 1-(2-chloro-phenyl)-piperazine in 300 ml of tetrahydrofuran was treated with 22 ml (0.16 mol) of triethylamine and 11.5 g (0.031 mol) of 5-bromomethyl-pyrimidine-2,4-diamine dihydrobromide and the mixture was stirred at room temperature under argon for 16 hours. The suspension obtained was suction filtered and the filtrate was completely freed from the solvents. The residue was chromatographed over silica gel with acetonitrile/methanol 1:1 as the eluent and digested in diethyl ether. 5.5 g (55%) of 5-[4-(2-chloro-phenyl)-piperazin-1-ylmethyl]-pyrimidine-2,4-diamine were obtained as beige crystals; m.p. 2:30°–235°.

EXAMPLE 41

5-[4-(2-Methoxy-phenyl)-piperazin-1-ylmethyl]-pyrimidine-2,4-diamine

A solution of 3.2 g (0.017 mol) of 1-(2-methoxy-phenyl)-piperazine in 100 ml of tetrahydrofuran was treated with 11.6 ml (0.084 mol) of triethylamine and 6.1 g (0.017 mol) of 5-bromomethyl-pyrimidine-2,4-diamine dihydrobromide and the mixture was stirred at room temperature under argon for 16 hours. The suspension obtained was suction filtered and the filtrate was completely freed from the solvents. The residue was chromatographed over silica gel with acetonitrile/methanol 1:1 as the eluent and digested in diethyl ether. 2.0 g (38%) of 5-[4-(2-methoxy-phenyl)-piperazin-1-ylmethyl]-pyrimidine-2,4-diamine were obtained as white crystals; m.p. 195°–196°.

EXAMPLE 42

5-(4-Phenyl-3,6-dihydro-2H-pyridin-1-ylmethyl)-pyrimidine-2,4-diamine a) A solution of 1.0 g (0.0051 mol) of 4-phenyl-1,2,3,6-tetrahydro-pyridine hydrochloride in 40 ml of dimethylformamide was treated with 2.13 ml (0.0153 mol) of triethylamine and 0.62 g (0.00170 mol) of 5-bromomethylpyrimidine-2,4-diamine dihydrobromide and the mixture was stirred at room temperature under argon for 65 hours. The mixture was completely freed from the solvents. The residue was chromatographed over silica with methanol as the eluent, digested in dichloromethane/water 1:1 and subsequently filtered off under suction. The organic phase was then completely freed from the solvents and the residue was digested in diethyl ether and subsequently filtered off under suction. A total of 0.27 g (56%) of 5-(4-phenyl-3,6-dihydro-2H-pyridin-1-ylmethyl)-pyrimidine-2,4-diamine was obtained as white crystals; m.p. 239°–241°.

b) 0.23 g (0.00081 mol) of 5-(4-phenyl-3,6-dihydro-2H-pyridin-1-ylmethyl)-pyrimidine-2,4-diamine was dissolved in 220 ml of hot methanol. The solution was treated at room temperature with 0.47 ml (0.00162 mol) of 3.5N ethanolic hydrochloric acid. The solution was completely freed from the solvents and the residue was recrystallized from methanol/diethyl ether. 0.23 g (79%) of 5-(4-phenyl-3,6-dihydro-2H-pyridin-1-ylmethyl)-pyrimidine-2,4-diamine dihydrochloride was obtained as white crystals; m.p. 209°–211°.

EXAMPLE 43

5-[4-(4-Fluoro-phenyl)-3,6-dihydro-2H-pyridin-1-ylmethyl]-pyrimidine-2,4-diamine A solution of 3.6 g (0.020 mol) of 4-(4-fluoro-phenyl)-1,2,3,6-tetrahydro-pyridine in 100 ml of tetrahydrofuran was treated with 13.9 ml (0.10 mol) of triethylamine and 7.3 g (0.020 mol) of 5-bromomethyl-pyrimidine-2,4-diamine dihydrobromide and the mixture was stirred at room temperature under argon for 16 hours. The suspension obtained was suction filtered and the filtrate was completely freed from the solvents. The residue was chromatographed over silica gel with acetonitrile/methanol 1:1 as the eluent and digested in diethyl ether. 3.5 g (58%) of 5-[4-(4-fluoro-phenyl)-3,6-dihydro-2H-pyridin-1-ylmethyl]-pyrimidine-2,4-diamine were obtained as brownish crystals; m.p. 265°.

EXAMPLE 44

2,4-Dimethyl-5-(4-phenyl-3,6-dihydro-2H-pyridin-1-ylmethyl)-pyrimidine a) A solution of 0.276 g (0.0020 mol) of (2,4-dimethyl-pyrimidin-5-yl)-methanol in 5 ml of tetrahydrofuran was treated with 1.6 ml (0.00202 mol) of 1.29M butyllithium in hexane at −78° under argon. Then, a solution of 0.39 g (0.00204 mol) of 4-methyl-benzene sulphonylchloride in 3 ml of tetrahydrofuran was added dropwise thereto, the temperature was left to rise to 0° and then a suspension of 0.403 g (0.00206 mol) of 4-phenyl-1,2,3,6-tetrahydropyridine hydrochloride and 1.1 ml (0.0080 mol) of triethylamine in 3 ml of tetrahydrofuran was added dropwise thereto. The mixture was stirred at room temperature for 3 hours, suction filtered and the filtrate was completely freed from the solvents. The residue was partitioned between dichloromethane and water, extracted, chromatographed over silica gel with ethyl acetate as the eluent. 0.31 g of a pale yellowish solid was obtained.

b) The product (0.28 g) was dissolved in 10 ml of ethanol and treated with 0.29 ml (0.0010 mol) of 3.5N ethanolic hydrochloric acid. The solution was completely freed from the solvents and the residue was recrystallized from acetonitrile/diethyl ether. 0.25 g (44%) of 2,4-dimethyl-5-(4-phenyl-3,6-dihydro-2H-pyridin-1-ylmethyl)-pyrimidine hydrochloride was obtained as white crystals; m.p. 176°–178°.

EXAMPLE 45

5-[6-(4-Chlorophenyl)-3,4-dihydro-1H-isoquinolin-2-ylmethyl]-2-methyl-pyrimidin-4-ylamine a) Firstly 0.22 ml (0.00160 mol) of triethylamine and then 0.26 ml (0.00155 mol) of trifluoromethanesulphonic anhydride were added dropwise under argon to an ice-cold solution of 0.38 g (0.00152 mol) of tert.-butyl 6-hydroxy-3,4-dihydro-1H-isoquinoline-2-carboxylate in 7.5 ml of dichloromethane. The mixture was stirred at room temperature for 1 hour, poured into saturated sodium hydrogen carbonate solution, extracted with ethyl acetate and completely freed from the solvents. 0.66 g of oily crude tert.-butyl 6-(trifluoromethanesulphonyloxy)-3,4-dihydro-1H-isoquinoline-2-carboxylate was obtained.

b) A solution of 0.66 g of crude tert.-butyl 6-(trifluoromethanesulphonyloxy)-3,4-dihydro-1H-isoquinoline-2-carboxylate in 5 ml of dimethoxyethane was treated under argon with 0.29 g (0.0018 mol) of 4-chlorophenylboric acid and 2.1 ml (0.0041 mol) of an aqueous 2N sodium hydrogen carbonate solution. The mixture was saturated with argon, 0.088 g (0.000076 mol) of tetrakis-(triphenyl-phosphine)-palladium was added and the mixture was boiled at reflux for 19 hours. The mixture was cooled, poured into 9 ml of an aqueous 2N sodium hydroxide solution and extracted with ethyl acetate. The residue was chromatographed over silica gel with cyclohexane/ethyl acetate 9:1 as the eluent. 0.52 g (100%) of a pale yellow oil was obtained. An analytical sample was recrystallized several times from hot n-hexane and gave tert.-butyl 6-(4-chlorophenyl)-3,4-dihydro-1H-isoquinoline-2-carboxylate as white crystals; m.p. 88.5°–90.5°.

c) A stream of hydrogen chloride gas was conducted through a solution of 2.52g (0.0073 mol) of tert.-butyl 6-(4-chlorophenyl)-3,4-dihydro-1H-isoquinoline-2-carboxylate in 110 ml of ethyl acetate. The reaction was followed by thin-layer chromatography. The mixture was cooled to 0° and suction filtered. 2.05 g (100%) of 6-(4-chlorophenyl)-3,4-dihydro-1H-isoquinoline hydrochloride were obtained as white crystals; sublimation at 215°–245° (dec.).

d) A suspension of 1.69 g (0.0087 mol) of 5-chloromethyl-2-methyl-pyrimidin-4-ylamine hydrochloride in 95 ml of dimethylformamide was treated with 2.035 g (0.00726 mol) of 6-(4-chlorophenyl)-1,2,3,4-tetrahydro-isoquinoline hydrochloride and 3.35 ml (0.0;24 mol) of triethylamine and stirred at room temperature under argon for 66 hours. The mixture was completely freed from the solvents. The residue was partitioned between dichloromethane and water. 16 ml of a 1N aqueous sodium hydroxide solution were added dropwise thereto, the mixture was extracted and chromatographed over silica gel with ethyl acetate/isopropyl alcohol 9:1 as the eluent and digested in diethyl ether. 2.0 g (63%) of 5-[6-(4-chlorophenyl)-3,4-dihydro-1H-isoquinolin-2-ylmethyl]-2-methyl-pyrimidin-4-ylamine were obtained as a white solid. An analytical sample was recrystallized from ethyl acetate and gave white crystals; m.p. 205°–208°.

e) A solution of 0.56 g (0.00053 mol) of crude 5-[6-(4-chlorophenyl)-3,4-dihydro-1H-isoquinolin-2ylmethyl]-2-methyl-pyrimidin-4-ylamine in 100 ml of ethanol was filtered and treated with 1.1 ml (0.00385 mol) of 3.5N ethanolic hydrochloric acid. The suspension obtained was suction filtered. 0.098 g (14%) of 5-[6-(4-chlorophenyl)-3,4-dihydro-1H-isochinolin-2-ylmethyl]-2-methyl-pyrimidin-4-ylamine dihydrochloride was obtained as white crystals; m.p. 223°–235° (dec).

EXAMPLE 46

5-[6-(3,5-Dichlorophenyl)-3,4-dihydro-1H-isoquinolin-2-ylmethyl]-2-methyl-pyrimidin-4-ylamine a) Firstly 1.46 ml (0.0105 mol) of triethylamine and then 1.7 ml (0.0102 mol) of trifluoromethanesulphonic anhydride were added dropwise under argon to an ice-cold solution of 2.49 g (0.010 mol) of tert.-butyl 6-hydroxy-3,4-dihydro-1H-isoquinoline-2-carboxylate in 80 ml of dichloromethane. The mixture was stirred at room temperature for 1 hour, poured into saturated sodium hydrogen carbonate solution, extracted with ethyl acetate and completely freed from the solvents. 3.81 g of oily crude tert.-butyl 6-(trifluoromethanesulphonyloxy)-3,4-dihydro-1H-isoquinoline-2-carboxylate were obtained.

b) A solution of 3.81 g of crude tert.-butyl 6-(trifluoromethanesulphonyloxy)-3,4-dihydro-1H-isoquinoline-2-carboxylate in 40 ml of dimethoxyethane was treated under argon with 2.01 g (0.0105 mol) of 3,5-dichlorophenylboric acid and 13.5 ml (0.027 mol) of an aqueous 2N sodium hydrogen carbonate solution. The mixture was saturated with argon, 0.578 g (0.00050 mol) of tetrakis-(triphenylphosphine)-palladium was added thereto and the mixture was boiled at reflux for 20 hours. The mixture was cooled, poured into 120 ml of an aqueous 2N sodium hydroxide solution and extracted with ethyl acetate. The residue was chromatographed over silica gel with cyclohexane/ethyl acetate 9:1 as the eluent. 3.42 g (90%) of tert.-butyl 6-(3,5-dichlorophenyl)-3,4-dihydro-1H-isoquinoline-2-carboxylate were obtained as a pale yellow dense oil.

c) A stream of hydrogen chloride gas was conducted through a solution of 3.42 g (0.0904 mol) of tert.-butyl 6-(3,5-dichloro-phenyl)-3,4-dihydro-1H-isoquinoline-2-carboxylate in 180 ml of ethyl acetate. The reaction was followed by thin-layer chromatography. The mixture was cooled to 0° and suction filtered. 2.58 g (91%) of 6-(3,5-dichlorophenyl)-3,4-dihydro-1H-isochinoline hydrochloride were obtained as white crystals; m.p. 220°–260° (dec.).

d) A suspension of 1.85 g (0.0095 mol) of 5-chloromethyl-2-methyl-pyrimidin-4-ylamine hydrochloride in 105 ml of dimethylformamide was treated with 250 g (0.00795 mol) of 6-(3,5-dichlorophenyl)-1,2,3,4-tetrahydro-isoquinoline hydrochloride and 3.66 ml (0.026 mol) of triethylamine and stirred at room temperature under argon for 65 hours. The mixture was completely freed from the solvents. The residue was partitioned between dichloromethane and water. 30 ml of a 1N aqueous sodium hydroxide solution were added dropwise thereto, the mixture was extracted and chromatographed over silica gel with ethyl acetate/isopropyl alcohol 9:1 as the eluent. Crystallization was then carried out, firstly from methanol/ethyl acetate/n-hexane and then from hot ethyl acetate. 1.21 g (38%) of 5-[6-(3,5-dichlorophenyl)-3,4-dihydro-1H-isoquinolin- 2-ylmethyl]-2-methyl-pyrimidin-4-ylamine were obtained as white crystals; m.p. 205°–211°.

EXAMPLE A

Tablets of the following composition are produced in the usual manner:

|  | mg/tablet |
|---|---|
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Table weight | 250 |

EXAMPLE B

Tablets of the following composition are produced in the usual manner:

|  | mg/tablet |
|---|---|
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Table weight | 400 |

EXAMPLE C

Capsules of the following compositions are produced:

|  | mg/capsule |
|---|---|
| Active ingredient | 50 |
| Crys. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The finished mixture is filled into hard gelatine capsules of suitable size.

We claim:

1. A compound of the formula

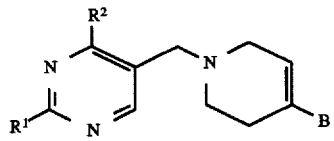

wherein
B is

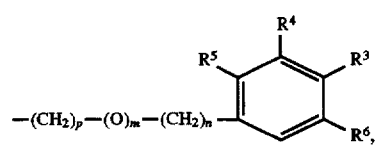

lower-alkyl, styryl, phenylethynyl or benzoyloxy-lower-alkyl;

$R^1$ and $R^2$ is independently, lower-alkyl or amino;

$R^3$–$R^6$ is independently, halogen, lower-alkyl, trifluoromethyl, lower-alkoxy or nitro;

n is 0, 1 or 2, and
m, p are, independently, 0 or 1.

2. A compound of the formula

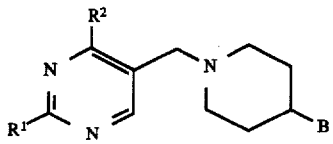

wherein
B is

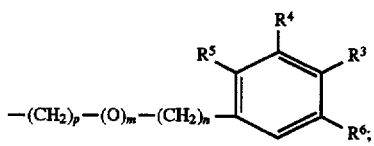

R¹ and R² is independently, lower-alkyl or amino;
R³–R⁶ is independently, hydrogen, halogen, lower-alkyl, trifluoromethyl, lower-alkoxy or nitro;
n is 0, 1 or 2, and
m, p are, independently, 0 or 1.

3. A compound of the formula

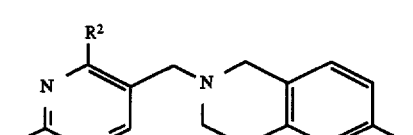

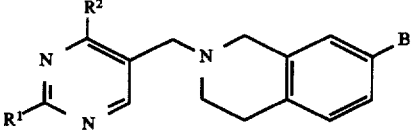

or

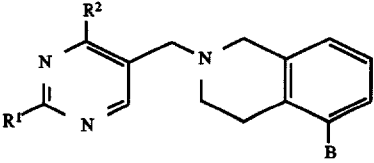

wherein
B is hydrogen,
or unsubstituted phenyl;
R¹ is methyl;
R² is amino.

4. A compound of the formula

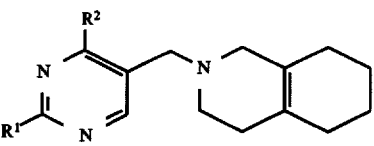

wherein
R¹ and R² is lower-alkyl or amino.

5. A compound according to claim 1, wherein R¹ is methyl, R² is amino and B is benzylmethyl, styryl or phenyl substituted by chlorine or methoxy.

6. A compound according to claim 5, selected from the group

5-[4-(4-chloro-phenyl)-3,6-dihydro-2H-pyridin-1-ylmethyl]-2-methyl-pyrimidin-4-ylamine, 5-[4-(4-methoxy-phenyl)-3,6-dihydro-2H-pyridin-1-ylmethyl]-2-methyl-pyrimidin-4-ylamine, 2-methyl-5-(4-phenethyl-3,6-dihydro-2H-pyridin-1-ylmethyl)-pyrimidin-4-ylamine and (E)-2-methyl-5-(4-styryl-3,6-dihydro-2H-pyridin-2-ylmethyl)-pyrimidin-4-ylamine.

7. A compound according to claim 3, selected from the group 5-(3,4,5,6,7,8-hexahydro-1H-isoquinolin-2-ylmethyl)-2-methyl-pyrimidin-4-ylamine and 2-methyl-5-(6-phenyl-3,4-dihydro-1H-isoquinolin-2-ylmethyl)-pyrimidin-4-ylamine.

8. A compound according to claim 4, wherein R¹ is methyl and R² is amino.

9. A pharmaceutical composition comprising a compound of the formula

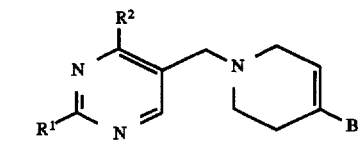

wherein
B is

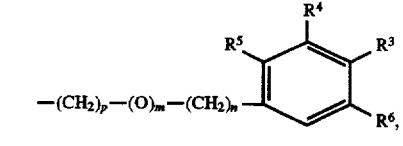

lower-alkyl, styryl, phenylethynyl or benzoyloxy-lower-alkyl;

R¹ and R² is independently, lower-alkyl or amino;
R³–R⁶ is independently, halogen, lower-alkyl, trifluoromethyl, lower-alkoxy or nitro;
n is 0, 1 or 2, and
m, p are, independently, 0 or 1.

10. A pharmaceutical composition comprising a compound of the formula

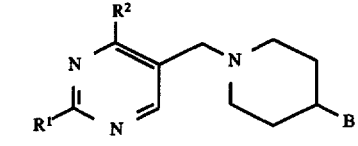

wherein
B is

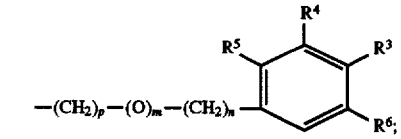

R¹ and R² is independently, lower-alkyl or amino;
R³–R⁶ is independently, hydrogen, halogen, lower-alkyl, trifluoromethyl, lower-alkoxy or nitro;
n is 0, 1 or 2, and
m, p are, independently, 0 or 1.

11. A pharmaceutical composition comprising a compound of the formula

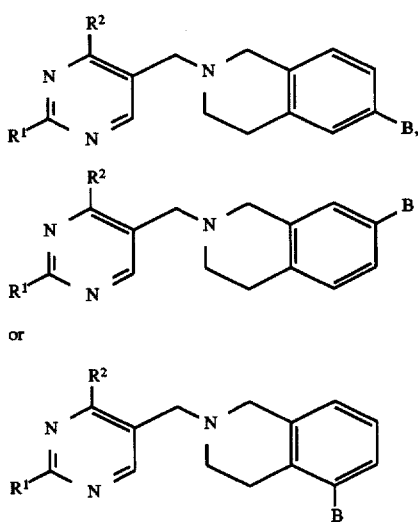

wherein

B is hydrogen, or unsubstituted phenyl;

R¹ is methyl;

R² is amino.

12. A pharmaceutical composition comprising a compound of the formula

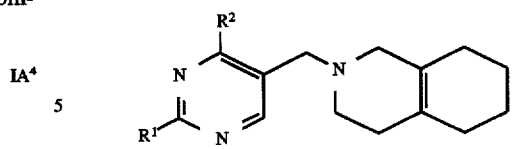

wherein

R¹ and R² is lower-alkyl or amino.

13. A pharmaceutical composition according to claim 9, wherein R¹ is methyl, R² is amino and B is benzylmethyl, styryl or phenyl substituted by chlorine or methoxy.

14. A pharmaceutical composition according to claim 13, wherein the compound is selected from the group 5-[4-(4-chloro-phenyl)-3,6-dihydro-2H-pyridin-1-ylmethyl]-2-methyl-pyrimidin-4-ylamine, 5-[4-(4-methoxy-phenyl)-3,6-dihydro-2H-pyridin-1-ylmethyl]-2-methyl-pyrimidin-4-ylamine, 2-methyl-5-(4-phenethyl-3,6-dihydro-2H-pyridin-1-ylmethyl)-pyrimidin-4-ylamine and (E)-2-methyl-5-(4-styryl-3,6-dihydro-2H -pyridin-2-ylmethyl)-pyrimidin-4-ylamine.

15. A pharmaceutical composition according to claim 11, wherein the compound is selected from the group 5-(3,4,5,6,7,8-hexahydro-1H-isoquinolin-2-ylmethyl)-2-methyl-pyrimidin-4-ylamine and 2-methyl-5-(6-phenyl-3,4-dihydro-1H-isoquinolin-2-ylmethyl)-pyrimidin-4-ylamine.

16. A pharmaceutical composition according to claim 12, wherein R¹ is methyl and R² is amino.

* * * * *